United States Patent [19]

Childress et al.

[11] Patent Number: 4,623,354
[45] Date of Patent: Nov. 18, 1986

[54] MYOELECTRICALLY CONTROLLED ARTIFICIAL HAND

[75] Inventors: Dudley Childress, Wilmette; John Strysik, Chicago, both of Ill.

[73] Assignee: Northwestern University, Evanston, Ill.

[21] Appl. No.: 736,599

[22] Filed: May 21, 1985

Related U.S. Application Data

[63] Continuation-in-part of Ser. No. 663,154, Oct. 22, 1984.

[51] Int. Cl.[4] .............................................. A61F 1/06
[52] U.S. Cl. ..................................................... 623/25
[58] Field of Search ................... 623/24, 25

[56] References Cited

U.S. PATENT DOCUMENTS

| | | | |
|---|---|---|---|
| 3,735,425 | 5/1973 | Hoshall et al. | 623/25 |
| 4,149,278 | 4/1979 | Wiker et al. | 623/24 |
| 4,246,661 | 1/1981 | Pinson | 623/25 |
| 4,314,379 | 2/1982 | Tanie et al. | 623/25 |

*Primary Examiner*—Leo P. Picard
*Attorney, Agent, or Firm*—Welsh & Katz, Ltd.

[57] ABSTRACT

A myoelectrically controlled artificial hand is provided having a pair of fingers extending distally from a pivot and mounted thereon for selective separation and conversions by means of a pair of electrical motors. The first electric motor has high speed and low torque with a drive train connected to one of the fingers so as to affect rapid separation and conversion of the fingers. The second motor has low speed and high torque, and has a drive train connected to the second finger to effect pinch force between the fingers. A field effect transistor driver actuates the electric motor to operate the artificial hand. The control mechanism for the motors is actuated by myoelectric signals from the user, so as to supply myoelectric pulses to the field effect transistor driver. As a result, the user can selectively separate or converge the fingers based on his own muscular movement. The combination of the field effect transistor driver and the pair of electric motors results in a highly efficient system which utilizes a minimal quantity of electric current, so that a single nine volt disposable battery may be used to power the system.

13 Claims, 10 Drawing Figures

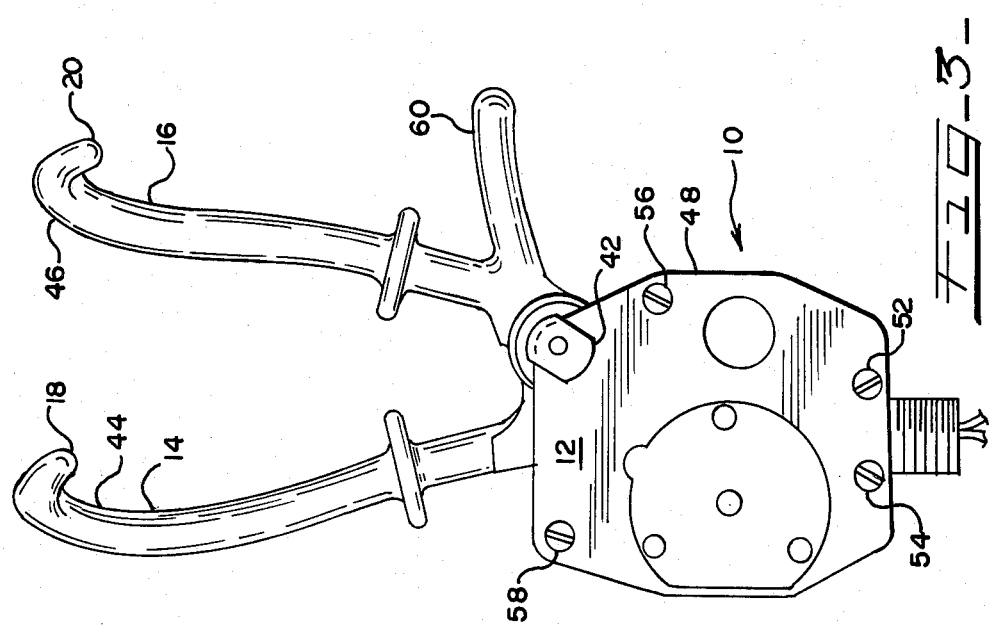
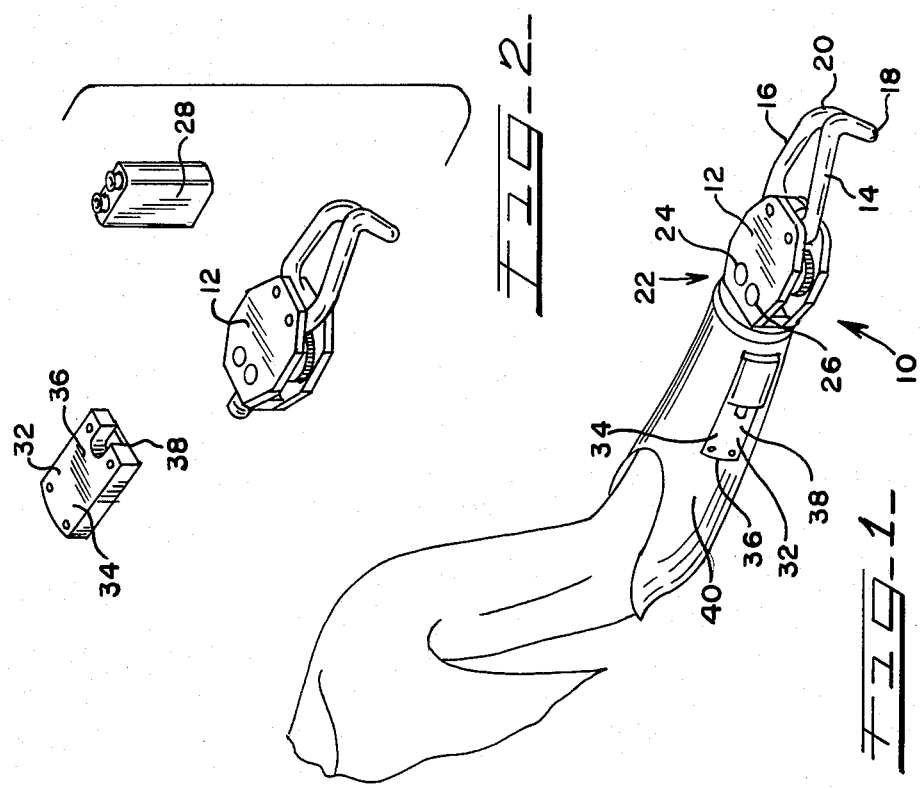

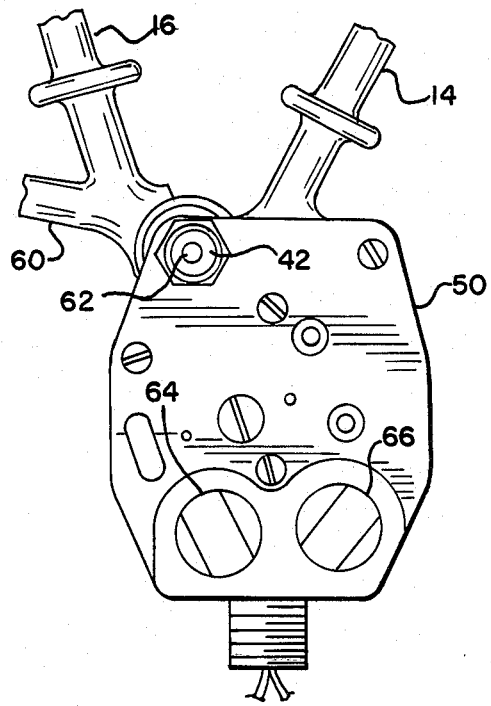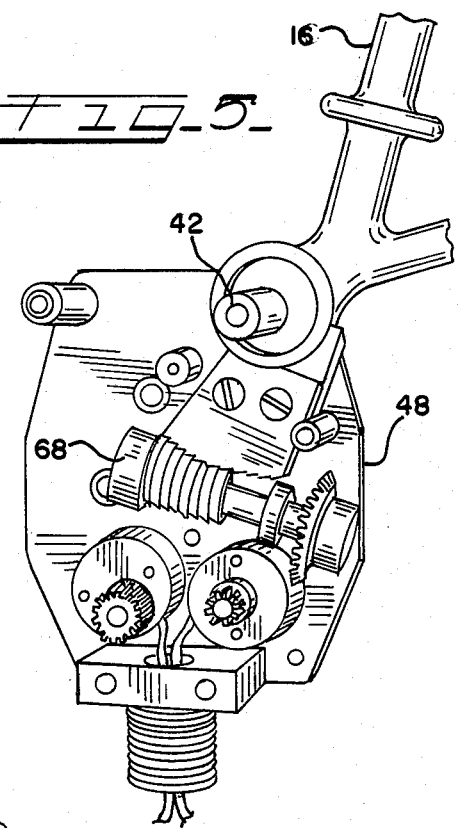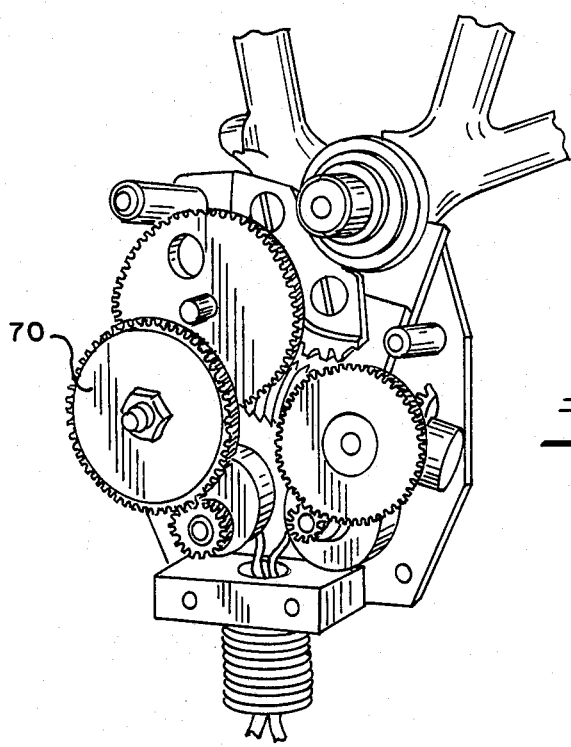

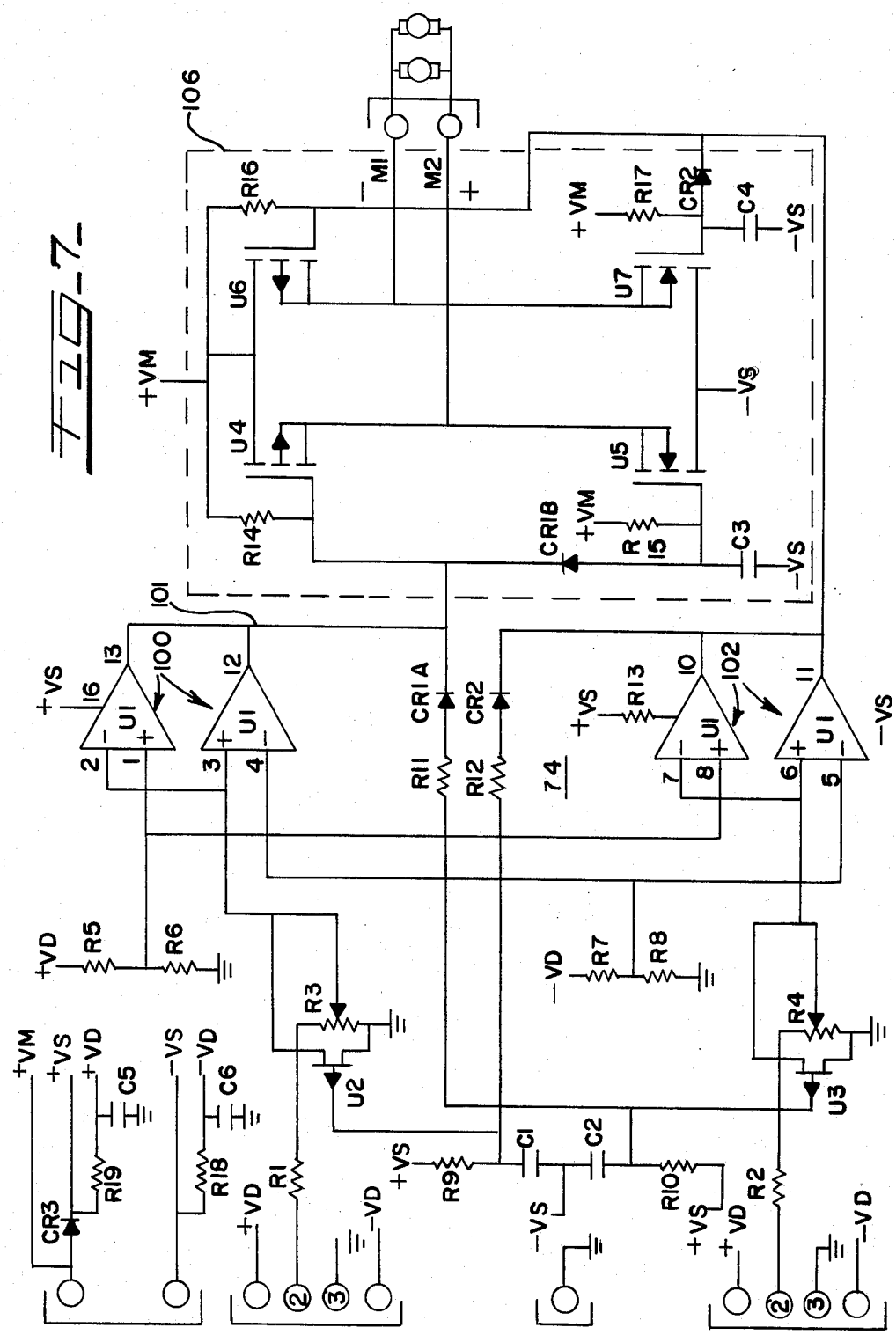

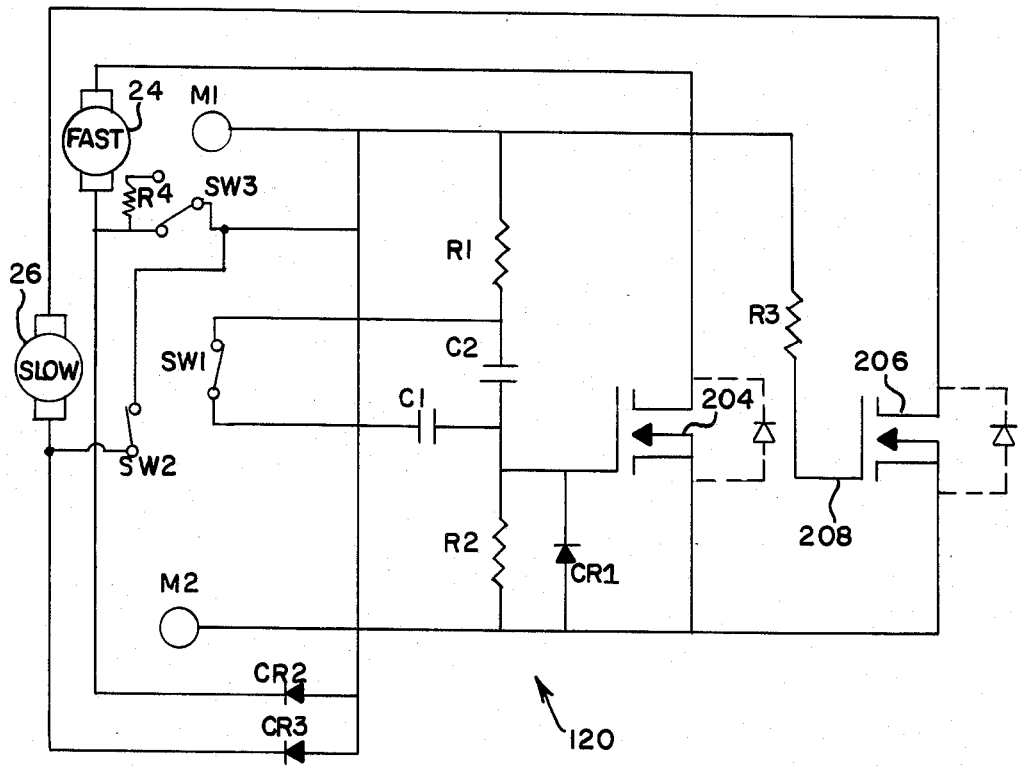
FIG-8-
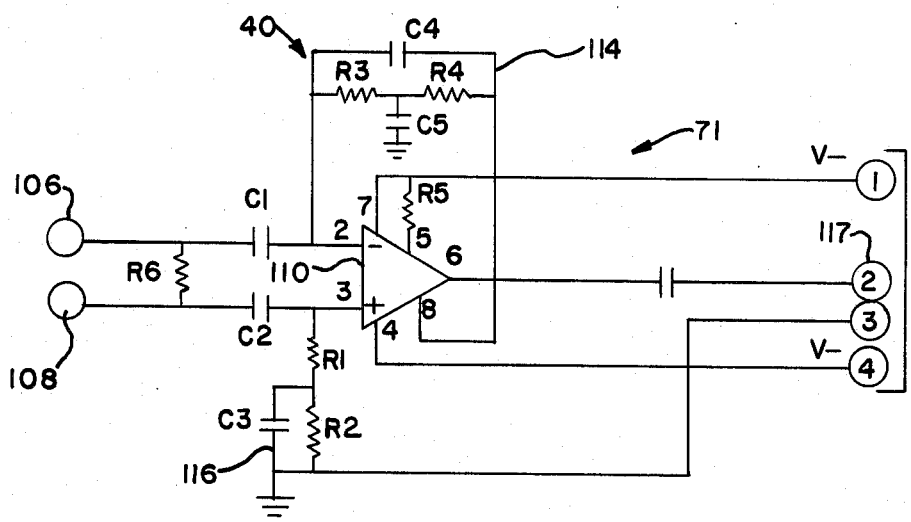
FIG-10-

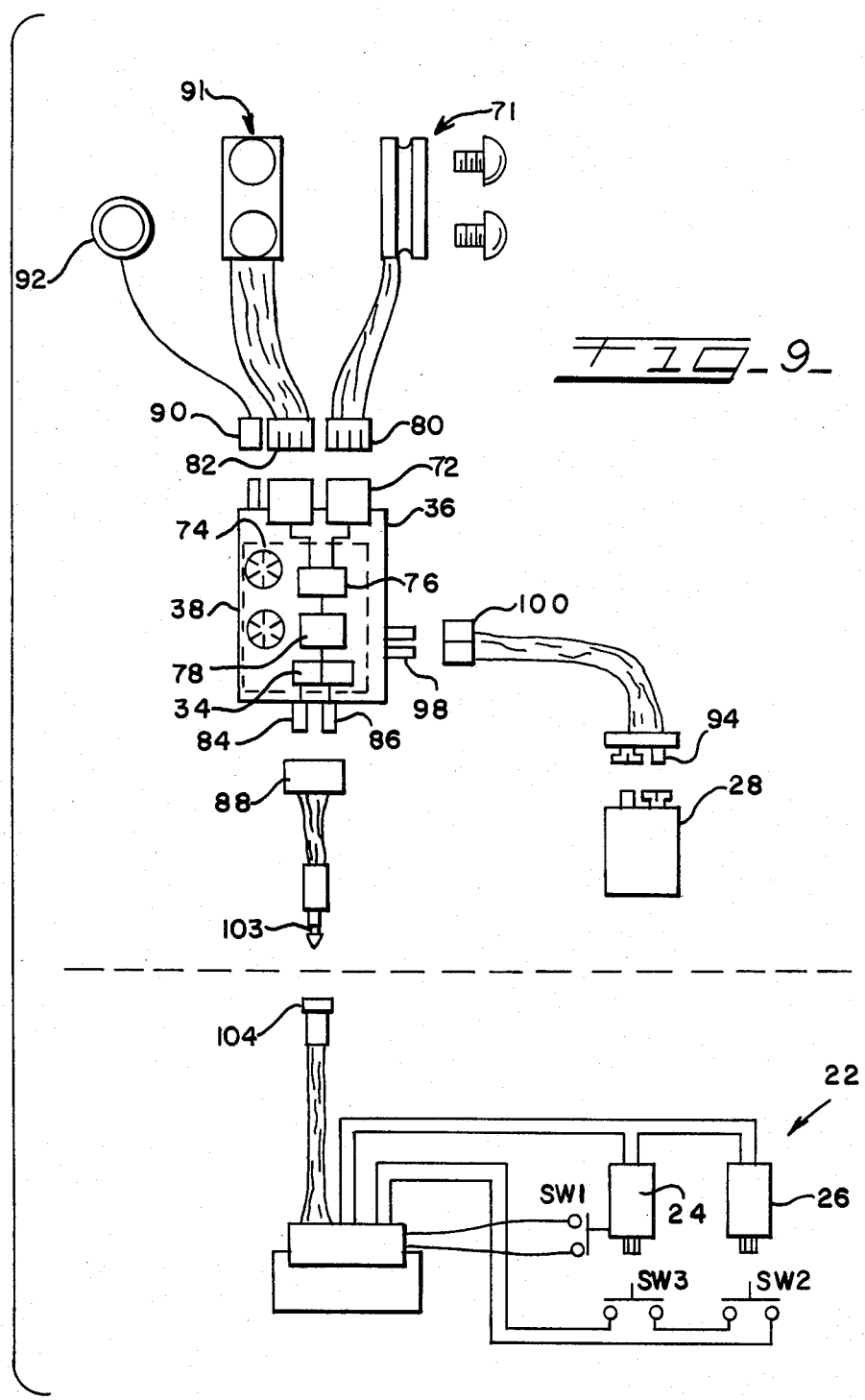

MYOELECTRICALLY CONTROLLED ARTIFICIAL HAND

The U.S. government has rights in this invention pursuant to funding under grant V101(134) P-5 and P-326 from the Veterans Administration.

The application is a continuation-in-part of U.S. patent application Ser. No. 663,154 filed Oct. 22, 1984 which is hereby incorporated by reference.

BACKGROUND OF THE INVENTION

The present invention relates generally to prosthetic devices and in particular to myoelectrically controlled hook/hand systems for amputees.

In 1972, the first electrically powered hook utilizing synergetic prehension was constructed by D. S. Childress (*Proceedings of the Fourth International Symposium of the External Control of Human Extremities*, Dubrovnik, 1972). The electrically powered hook disclosed therein, developed by one of the present inventors, utilizes a two motor system driven by a bipolar transistor driver for selectively separating or converging two fingers which extend from a pivot. Control of the motors is effected through electrodes placed on voluntary muscles of the patient.

The use of bipolar transistors in myoelectric devices may be seen generally in U.S. Pat. Nos. 3,883,900, 3,641,993, 3,501,776, and the article "EMG Operated Electronic Artificial Leg Controller" by Saxena, published in *Medical and Biological Engineering and Computer*, September, 1977. However, the prior art does not reveal the use of field effect transistors in artificial limb type prosthetic devices.

In an article entitled "Artificial Hand Mechanism," published in *The American Society of Mechanical Engineers* in 1972, one of the present inventors disclosed the concept of synergetic prehension; wherein two motors are used for controlling an artificial hand. One of the motors is used for high-speed opening and closing of one of the pair of fingers utilized in the hand. The other motor is geared for high torque so as to apply relatively greater pinching force when the two fingers converge together for gripping of objects. Similarly, in the "Bulletin of Prosthetics Research," published Fall, 1974, one of the present inventors disclosed the concept of myopulse modulation. In myopulse modulation, the processing scheme consists of amplication of a myoelectric signal in conjunction with a small threshold. Positive and negative pulses of the myoelectric signal are amplified to saturation and an inverting stage is added to invert either the positive or negative pulses to obtain a pulse train of all positive or all negative pulses. However, a problem with this system is the relatively high quiescent electric current which requires a relatively larger size battery source.

The present invention utilizes field effect transistors to effect a significant savings of electric power. The use of field effect transistors in implanted devices, such as pacemakers, may be seen in U.S. Pat. No. 4,285,345. However, the current requirements of a pacemaker are vastly different from that of an artificial prosthetic device in which a pair of fingers must be separated by an electric motor and operated with sufficient torque to grasp an object firmly. Thus, the present design for a field effect transistor driver utilized in a myoelectrically controlled hook/hand device represents a non-obvious improvement over the prior art.

BRIEF SUMMARY OF THE INVENTION

A myoelectrically controlled artificial hand is provided in the present invention which includes a pivot member having a pair of fingers extending distally therefrom. The fingers are pivotally mounted so as to be selectively separated or converged together at their distal ends. A pair of electric motors are used for effecting the selective separation of the fingers. A high speed low torque electric motor having a drive train connected to a first one of the fingers is constructed and arranged to effect rapid separation or convergence of the fingers. A second high torque low speed electric motor has a second drive train connected to a second one of the fingers. The second motor is constructed and arranged to effect high pinch force between the fingers. A battery is used for supplying electric power to the electric motor. Field effect transistor drivers actuate the electric motors when supplied with myoelectric pulses of a specified band width. The FET's reduce the electric power necessary to operate the myoelectrically controlled hand. A control mechanism is further provided for supplying myoelectric pulses to the field effect transistor drivers in response to myoelectric signals generated by the user. As a result, the fingers may be selectively separated or converged.

Through the use of field effect transistors, a unique damping effect may be implemented in the mechanism controlling the artificial fingers. Thus, movement of the artificial fingers may be selectively dampened in order to position the fingers at a desired location. This allows the fingers to be opened to a desired degree and not coast to a full open position, thereby allowing more precise use of the fingers. Also, through the use of field effect transistors, an undamping circuit can be provided for the high torque motor so that the finger connected to the high torque motor coasts when returning to an open position.

BRIEF DESCRIPTION OF THE DRAWINGS

FIG. 1 of the drawings is a front perspective view of a myoelectrically controlled artificial hand.

FIG. 2 of the drawings is an exploded view of the hand portion, the battery portion and the control circuitry of the myoelectric hand of FIG. 1.

FIG. 3 of the drawings is a bottom view of the artificial hand of FIG. 1.

FIG. 4 of the drawings is a top view of the artificial hand of FIG. 1.

FIG. 5 of the drawings is a bottom view of the artificial electric hand of FIG. 3, shown partially disassembled.

FIG. 6 of the drawings is a bottom view of the artificial hand of FIG. 3, partially disassembled and showing in particular a gear train mechanism.

FIG. 7 of the drawings is a schematic electrical diagram of one embodiment of the circuitry that may be employed in the myoelectric hand of FIG. 1.

FIG. 8 of the drawings is a schematic diagram of a portion of the cutoff and damping circuitry of the myoelectric hand of FIG. 1.

FIG. 9 of the drawings is a schematic diagram of the voluntary opening/closing prehension device of FIG. 1, showing in particular an electrode, a myoprocessor, a battery selectively separable from the myoprocessor circuit, a cut-off and damping controller circuit and motors selectively attachable to the myoprocessor circuit.

FIG. 10 of the drawings is a schematic diagram of the electrical circuitry for an electrode adapted for use with the myoelectric hand of FIG. 1.

DETAILED DESCRIPTION OF THE PREFERRED EMBODIMENT

Referring now to the drawings, and in particular to FIG. 1, a voluntary opening/closing prehension device 10 is shown. Voluntary opening/closing prehension device 10 is an artificial hand, which opens in response to a myoelectric signal from the patient, and which closes in response to a myoelectric signal from the patient.

Voluntary opening/closing prehension device 10 comprises a pivot member 12 having a pair of fingers 14 and 16 extending distally therefrom. When fingers 14 and 16 are pivoted, distal end 18 of finger 14 is either separated or converged against distal end 20 of finger 16.

Electric motor mechanism 22 (best seen in FIG. 5) is used for selectively separating fingers 16 and 18. Specifically, electric motors 24 and 26 are used to pivot fingers 14 and 16 so as to cause separation or convergence of distal ends 18 and 20. Battery 28 is electrically connected to electric motor mechanism 22. Battery 28 supplies electric power to electric motors 24 and 26. A field effect transistor driver mechanism 34 which is attached to circuit board 36 is used for actuating electric motor mechanism 22. By this it is meant that an electric signal is sent from field effect transistor driver mechanism 34 to electric motor mechanisms 22 causing motor mechanisms 22 to move fingers 16 and 18. Field effect transistor driver mechanism 34 also serves, at least in part, to limit actuation of electric motor mechanisms 22 to those instances when a signal of a specified threshold strength or greater is received from control mechanism 38. Field effect transistor driver mechanism 34 and control mechanism 38 are also located on circuit board 36. Thus, control mechanism 38 receives a myoelectric signal from the patient and translates it into a myoelectric pulse which in turn actuates electric motor mechanism 22.

Pivot member 12 is mounted on artificial forearm 40 which in turn is mounted on the arm of the patient. As seen in FIG. 1 of the embodiment shown, battery member 28 is mounted in artificial forearm 40 as is field effect transistor driver mechanism 34. As seen in FIG. 2 of the drawings, pivot member 12 is detachable from forearm member 40. In addition, battery 28 is also removable and detachable from forearm member 40. Similarly, field effect transistor driver mechanism 34 is also removable and detachable from forearm member 40.

Turning now to FIG. 3 of the drawings, additional detail of myoelectric hand 10 and pivot 12 in particular may be seen. Fingers 14 and 16 are pivotally mounted on pivot 12, with finger 16 being pivotally mounted on pin 42. It may be further seen in FIG. 3 that fingers 14 and 16 are curved inwardly in order to facilitate grasping of objects at their respective distal ends 18 and 20. In addition, fingers 14 and 16 have flattened interior surfaces 44 and 46 for the grasping of objects therebetween. Pivot 12 is actually made up of a pair of plates, one of which, plate 48, is shown in FIG. 3. Plate 48 is attached to plate 50, shown in FIG. 4, by means of a plurality of screw members 52-58 respectively. As further seen in FIG. 3, a thumblike appendage 60 extends from finger 16.

Turning now to FIG. 4 of the drawings, plate 50 includes an aperture 62 adapted for telescopic reception of and rotatable connection with pin 42. Plate 50 further includes sockets 64 and 66 adapted for reception of electric motors 26 and 24, as best seen in FIG. 5.

Turning now to FIG. 5, motor 26 extends from plate 48 and is connected by means of worm gear mechanism 68 to finger 16 so as to selectively effect pivotal movement of finger 16.

As seen in FIG. 6, electric motor 24 is connected by means of gear train 70 to pivotal finger 14. Thus, selective actuation of electric motors 24 or 26 causes fingers 14 and 16 either to separate or converge.

Turning now to FIG. 9 control mechanism 38, incorporated in voluntary opening prehension device 10, is electrically connected to a plurality of electrodes such as electrodes 71. Each electrode 71, also referred to as a "myotrode," is affixed to the user proximate a voluntary muscle. Preferably, voluntary muscles in the forearm or upper arm of the patient may be used in order to more closely simulate normal functioning of the hand. Electrode 71 is connected by means of wires, to a coupling 72 on circuit board 36. Coupling 72 in turn is connected to myoprocessor circuit 74 which detects and processes the myoelectric signals from electrodes 71, as will be discussed in greater detail hereinafter. As previously mentioned, myoprocessor circuit 74 is connected to a battery such as battery 28. Myoprocessor circuit 74 includes complementary metal oxide semiconductor comparators 76 which serve to process the myoelectric signal into what is called a myopulse. A myopulse is an electric pulse suitable for actuating the field effect transistor driver 34.

The threshold 78 restricts generation of a myoelectric pulse to those instances in which the myoelectric signal from electrode 71 exceeds a predetermined threshold. It should be noted that the threshold 78 is established by a number of electrical components contained within the circuitry to be described herein. As a result of the aforesaid circuitry, when a strong voluntary muscle movement from the patient is detected by electrode 71, electric motors 24 and 26 are actuated so as to separate or converge fingers 14 and 16. As further seen in FIG. 9, field effect transistor drivers 34 and complementary metal oxide semiconductor comparators 76 are fixed to circuit board 36 which in turn is modular so as to be removable from voluntary opening prehension device 10. By modular it is meant that the components are connected to circuit board 36 by means of quick release plugs such as plugs 80, 82, 88 and 100. It should be noted in this regard that plug 90 is electrically connected to ground 92 so as to serve as a reference for the previously mentioned threshold. Battery 28 is also connected by means of plug 94 to corresponding plugs 98 and 100 on circuit board 36. Thus, battery 28 is selectively removable and replaceable from voluntary opening prehension device 10. As further seen in FIG. 9, circuit board 36 is connected to electric motor mechanism 22 by means of quick release plugs 103 and 104. In a preferred embodiment, quick release plugs 103 and 104 are positioned at the juncture between pivot 12 and forearm member 40. Thus, quick, easy and low cost disconnection of pivot member 12 is provided.

As mentioned in parent patent application Ser. No. 663,154, artificial forearm member 40 is attached to the arm of the patient. Preferably forearm member 40 is formed as a plastic housing which contains the aforesaid circuit board 36 and battery 28. Forearm 40 may be constructed of a variety of plastic materials or natural materials as is commonly known in the art. In addition, forearm 40 may be attached to the natural arm of the patient by either a vacuum mechanism or a contour mechanism in the proximal end of the forearm 40, again as commonly known in the art.

One of the features of the present invention, best seen in FIGS. 5, 6 and 9, is the use of a dual motor system to obtain high speed and prehension as well as high force in gripping. The CMOS myoelectric circuitry and VMOS FET drive transistors, has low quiescent current, few parts, wide operating voltage and the ability to have both high speed prehension and firm gripping. The present myoelectric hand also utilizes one nine-volt battery as shown in U.S. patent application Ser. No. 663,154 filed Oct. 22, 1984, the parent of the present case.

The myoelectric hand 10 consists of a motor and gear arrangement with a back lock mechanism to keep the motor from being back driven by the fingers. Electric motor 24 is a high speed low torque electric motor connected by means of gear mechanism 70 to finger 14 which, when actuated, quickly opens or separates the fingers 14 and 16. The electric motor 26 is a low speed high torque electric motor connected to finger 16 which is constructed and arranged to effect a high pinch force between the fingers. As a result, through the use of a two motor system, both high pinch force and quick opening can be achieved. Similarly, the present invention utilizes field effect transistors to reduce the electrical requirements for operation of the device, thereby minimizing costs.

As a result of the aforesaid circuitry, a myoelectric hand is provided which has both high pinch force, high speed opening and closing, is highly efficient in the use of electricity so as to minimize power requirements, and utilizes field effect transistors to selectively damp the electric motors and their operation.

Turning now to FIG. 10 of the drawings, when a voluntary muscle is flexed, a myoelectric signal can be detected between the contact electrodes 106 and 108; for example, when a 100 microvolts RMS signal is generated by a voluntary muscle of the user, the myotrode circuit 71 produces a resulting output of 1 volt RMS. This amplification is accomplished by the CMOS operational amplifier 110 which in a preferred embodiment is an RCA, CA-3078 integrated circuit. Contacts 106 and 108 are capacitively coupled to the amplifier 110 by means of an RC network composed of C1, C2 and R6. The capacitors C1 and C2 are preferably Johansen No. 500R15W103KP and the resistor R6 is preferably a Mepco No. 9C-1206-3-A-1005-J-K-R. Connected to the operational amplifier 110 is a Bridge-T Network having two legs, 114 and 116. The first leg 114 includes capacitor C4 and the second leg includes capacitor C3, as shown. Capacitors C3 and C4 are Johansen No. 500R15N102JP's. First leg 114 is the feedback network for the operational amplifier 110. The function of second leg 116 is basically to balance operational amplifier 110. The operational amplifier 110 is capacitively coupled with the contact electrodes 106 and 108, and it is also capacitively coupled with the output 117. Resistor R6 sets the quiescent current for the operational amplifier 110. Instead of feeding back from the output of the operational amplifier 110 the system feeds back through the compensation network, as shown. As a result, amplifier 110 is more stable and has higher gain than can be obtained otherwise.

As best seen in FIG. 7 of the drawings, the output from myotrode circuits 71 as seen in FIG. 10 is coupled to the myoprocessor 74 through resistors R1 and R2 and into variable resistors R3 and R4 which serve as gain controls. The signal from variable resistor R3 is coupled to pins 2 and 3 of a dual comparator 100, as shown. The dual comparator 100 compares that signal to threshold voltages coupled to pins 1 and 4. Similarly, the signal from variable resistor R4 is applied to a dual comparator 102 at pins 6 and 7 and compared to threshold voltages coupled to pins 5 and 8. The signal that comes out of potentiometers R3 and R4 is an AC signal (approx. 0 to $/\pm 0.5_v$) that fluctuates between positive and negative (i.e., an amplified myoelectric signal with a mean of zero). The dual comparators 100 and 102 comprise CMOS amplifiers; again an Siliconix L161 is the preferred integrated circuit. Each of the comparators has a positive or a negative threshold. The positive threshold is determined by the voltage divider formed by the resistor R5, R6 and the negative threshold is determined by the voltage divider formed by the resistors R7, R8, as shown.

The output of the dual comparators 100, 102 are normally positive when the input myoelectric signal is zero or to low to trigger the comparators. However, when the positive threshold is exceeded, the output pin 13 of the comparator 100 goes negative. If the negative threshold is exceeded, pin 12 goes negative. Thus any time the absolute magnitude of the signal is greater than these thresholds, a negative pulse is generated at the output 101. This is called myopulse modulation. The thresholds are set relatively low; preferably 30 to 40 millivolts.

The negative signal pulses from the output 101 turn on the diode CR1A and are coupled through resistor R11 to a field effect transistor U3. These negative pulses turn on the field effect transistor U3, thereby shorting out the signal to the dual comparator 102 when the dual comparator 100 has been turned on. This effectively shuts off the comparator 102. The reason for shutting off the dual comparator 102 is that there is frequently a small signal involuntarily generated by nearby muscles when a muscle is voluntarily contracted. Thus, in order to prevent this signal from activating the other dual comparator 102 after the first comparator 100 has been activated, dual comparator 102 is shut off. This prevents the motors from being intermittently driven in both directions.

An RC network composed of resitor R9 and capacitor C1 is coupled to the gate of U2, and a network composed of R10 and C2 is coupled to the gate of U3 to provide a time delay. This maintains J FET's U2 or U3 in the on state following a signal change for a time period determined by the RC time constant, thereby preventing the J FET's U2 and U3 from rapidly turning on and off due to the pulsed signals from the comparators 100, 102.

The dual comparator 102 and J FET U2 function in the same manner as the dual comparator 100 and J FET U3 whenever a myoelectric signal is coupled to the resistor R2 from a myotrode located proximate another muscle. Thus, myoelectric signals coupled to the dual comparator 100 result in myopulse signals which can be used to activate the motors in one directions, and myoelectric signals coupled to the dual comparator 102 results in myopulse signals for activating the motors in the other direction.

Referring back to the dual comparator 100 in FIG. 7, the myopulse signals generated by the dual comparator 100 are coupled to a bridge 106 comprising field effect transistors U4, U5, U6 and U7. The transistors U5 and U7 are enhancement mode, n-type, MOS field effect transistors which are turned on when there are no myopulse signals from the dual comparators 100, 102 due to the pull-up resistors R15 and R17. These transistors provide damping for the motors when the motors are turned off. The transistors U4 and U6 are enhancement mode p-type MOS field effect transistors which are off when there are no myopulse signals from the dual comparators 100,102, due to pull-up resistors R14 and R16. This will result in zero voltage across the M1–M2 terminals during the no-signal condition. The resistors R15 and R17 are large value resistors (10MΩ in the illustrated embodiment) which keep the gates of the transistors U6 and U7 just above threshold, while resistors R14 and R16 are low value resistors (150KΩ in the illustrated embodiment) which pull the gates of the transistors U4 and U6 up to approximately the supply voltage $V_M$.

When negative myopulses are coupled from the output 101 through the diode CR1B, they pull down the gate of the field effect transistor U5, turning off the transistor U5. Due to the high resistance of R15, when the comparator 100 pulls down the gate of the field effect transistor U5, it will be discharged down very quickly, turning off the transistor U5 very quickly. At the same time, the gate of the FET U4, which is in the off state, will be pull down turning on the FET U4. Since the gate of U4 was initially near the supply voltage $V_M$, transistor U4 will turn on after the transistor U5 has turned off. This prevents U4 from turning on so fast that U5 is still on which would result in a very high current drain on the battery. Thus, the timing of switching of the transistors U4 and U5 is controlled by the size of the respective resistors R14 and R15.

Since the dual comparator 100 produces the signals that switch the transistors U4 and U5, dual comparator 102 is disabled by J-FET transistor U3 and therefore the transistors U6 and U7 will remain in their initial condition (i.e., U6 off, U7 on). Therefore, the FET U7 will couple the negative supply voltage $-V_s$ to M1 and the FET U4 will couple the positive supply voltage $V_M$ to M2 providing a voltage to drive the motors in one direction of approximately $V = V_M + V_s$. Similarly, when the comparator 102 is activated it generates myopulses which turn off the FET U7 and turns on the FET U6 producing a voltage across the M1–M2 terminals of approximately $V = (V_M + V_s)$ to drive the motors in the opposite direction.

The capacitors C3 and C4 in FIG. 7 should be noted. The strength of the contraction of the muscle determines the width of the myopulses which in turn controls the speed of the motors. The two P-type devices, U4 and U6 in FIG. 7, are turned on and off by these pulses, which controls the motor speed. But while the motor is running, damping on the motor is generally not desirable between the pulses. If the motor is allowed to coast between pulses jerking motion is avoided. As noted previously, field effect transistors U5 and U7 provide damping to the motors when the motors are off (i.e., when U5 and U7 are on). When one of the N-type FETs (i.e., U5 and U7) is turned off by a pulse, C3 in FIG. 7 associated with the FET U5 will keep it off for a short period of time which will bridge these gaps between the pulses so that it doesn't damp while the motors are running. C4 does the same thing with regard to the FET U7.

It should be further noted in FIG. 7 that the battery section shown in the upper left hand corner includes a diode CR3 provided to protect the circuit in case the battery is connected to reverse. The battery 28 is preferably nine volt transistor type battery. R19 and C5 and R18 and C6 provide decoupling for the myotrode and the threshold voltage sources $(-V_D, +V_D)$ for the comparators 100,102 to stabilize these voltages against fluctuations caused by the motors. There is no real ground or center tab from the battery. Ground is formed by the voltage dividers R5 and R6 and R7 and R8 and is connected to the ground electrode 92 (see FIG. 9) contacting the user's body.

As best seen in FIG. 8 of the drawings, cut off and damping controller 120 includes three switches; switches 1, 2 and 3. Switch 1 (SW1) is a magnetic reed switch for sensing whether the fast motor 24 is running. A magnet on the rotor of the fast motor 24, rotates when the rotor turns causing the magnetic reed switch (SW1) to open and close as the motor rotates. When the motor stops rotating in the closing direction, the circuitry of the cut-off and damping controller 120 detects the fact that switching has stopped and turns the power off to the fast motor 24. Switch 2 is a limit switch for the slow motor 26 in the open direction and switch 3 is a conventional toggle type limit switch for the fast motor 24 in the open direction.

Generally, the cut off and damping controller 120 performs several functions. The power is applied on terminals M1 and M2 from the myoprocessor 74 (see FIG. 7) with the polarity determined by whether the fingers 14,16 are opening or closing (e.g., when opening, M1 is negative, M2 positive). Thus, during opening, starting at the terminal M1, a current goes through switch 3, through the fast motor 24 and down to a VMOS FET 204, as shown. At this point, the FET 204 is turned off but because it is a VMOS FET, it has an internal diode from the source to the drain (shown schematically with dash lines) which conducts current around the control part of the FET 204. Thus, the current is conducted down through the source to M2, so that the circuit has been completed for the fast motor.

The slow motor 26 is activated similarly. Starting at M1, current flows down through switch 2, which is normally closed, through the slow motor 26, to a VMOS FET 206 and again through the internal diode and back to M2. At this point both motors have been turned on and they are opening the fingers. When the full open position of the fingers has been reached, switches 2 and 3 are mechanically opened by the fingers which breaks the circuit to the motor and turns off the current. Switch 3 has a resistor R4 across it, so that when switch 3 opens, the circuit is not totally open but a small current continues to flow to the fast motor 24 through the resistor R4. The reason for this is because the fast motor 24 is going very fast and when the finger hits the switch, if current was completely cut off, it would bounce off the switch. Resistor R4 applies a small current to the fast motor to keep it from bouncing off the switch. Thus, the fast motor is not completely turned off.

When closing the myoelectric hand, the polarity of M1 and M2 are reversed (i.e., M1 is positive and M2 is negative). Starting at M1 (considering the slow motor circuit first) current cannot go through the limit switches (SW2, SW3) because they are now open, thus current from M1 flows down through CR3, and up through the slow motor 26. The current path is then down to the FET 206 and since the gate 208 of the field effect transistor 206 is positive through R3, conduction is through the FET 206 itself and across to M2 thus completing the circuit. As a result, the slow motor is turned on and as soon as it starts running limit switch 2 is closed and the current path through CR3 is not longer needed. The slow motor 26 in closing will be powered as long as current is provided to it. There is no cut off on closing. The fast motor closes until it stalls when it hits the other finger, or, if grasping an object, as soon as it comes up against the object. As a result, for fast motor closing, starting at M1, the initial current path is down through CR2 and through the fast motor 24 until the motor 24 travels far enough to release the limit switch 3. The conduction path is then through switch 3 with the current going through the fast motor 24 and down to the drain of the FET 204. When the FET 204 is turned on, it conducts down to the source and over to M2. The FET 204 is first turned on when M1 goes from negative to positive creating a pulse of discharge current through R1, C2 and R2. R1 is 10KΩ, R2 is 10 MΩ so the gate of the FET 204 will see a positive pulse which turns the FET 204 on, starting the fast motor. C2 immediately begins to charge up which would turn the gate of FET 204 off, but as soon as the motor starts turning, magnetic reed switch 1 starts opening and closing. That puts positive pulses through R1, through switch 1, to C1, and to the gate of the FET 204. As long as the motor is turning, switch 1 is opening and closing, thereby applying positive pulses to the gate which keeps the FET 204 turned on. When the motor stalls, switch 1 stops opening and closing and either remains open or closed, depending on where it stops. C1 will then charge negative through R2 and the gate of the FET 204 will be negative and that turns the FET 204 off. This turns off current to the fast motor.

It is desirable when turning the fast motor 24 off to damp it so that it does not coast in either direction. It is also desirable to damp the slow motor 26 when it is closing so that when the signal is turned off, it stops. But in opening the slow motor 26, it is preferrable not to have damping so that the motor can coast. The reason it is desirable for the slow motor to coast in the opening direction is to get the slow finger to stay near its cut off switch and to do that every time and opening signal is given. The range of motion of the slow motor is relatively small whereas the range of motion of the fast motor is much greater and therefore that fast motor 24 must always be damped.

When the signal is turned off to the slow motor 26, the motor works like a generator producing a voltage. When the slow motor 26 is on and opening, current runs through the internal diode of FET 206 and out to the slow motor 26. When power is withdrawn, the slow motor tends to keep running in the same direction and acts like a generator to generate an output voltage with positive at the top of the slow motor 26 (see FIG. 8). The FET 206 is turned off and the internal diode is reversed biased so current cannot flow back through the circuit to be damped. When the slow motor 26 is operating to close the fingers, the voltages are reversed and then the current flows in the opposite direction through the slow motor, and through the internal diode of FET 206, which damps the motor. This assumes that the slow motor limit switch (SW2) is closed.

The fast motor 24 is preferrably damped in both directions. In the opening direction, current comes from the top of the fast motor 24 and then down through the internal diode of the FET 204 and out to form a complete path. In the other direction, current comes down to the FET 204 which is turned on by a positive voltage coupled through CR1. When the fast motor is turned off, the gate of FET 204 takes awhile to discharge the gate due to the high resistance of R2, thus producing damping. So in one direction, the FET 204 is actively turned on, and in the other direction, current passes through the internal diode. Fast motor 24 is thereby damped in both directions.

A specific embodiment of the novel myoelectrically controlled prehension device has been described for purposes of illustrating the manner in which the invention may be made and used. It should be understood that implementation of other variations and modifications of the invention in its various aspects will be apparent to those skilled in the art, and that the invention is not limited by the specific embodiments described. It is therefore contemplated to cover by the present invention any and all modifications, variations or equivalents that fall within the true spirit and scope of the basic underlying principles disclosed and claimed herein.

What is claimed is:

1. A myoelectrically controlled artificial hand comprising:
    a pivot member;
    a pair of finger members extending distally from said pivot member and pivotally mounted thereon for selective separation and convergence;
    electric motor means for effecting said selective separation and convergence of said finger members,
    said electric motor means including a high speed low torque electric motor having a first drive train connected to a first one of said finger members, constructed and arranged to effect rapid separation and convergence of said finger members; and
    a second high torque low speed electric motor having a second drive train connected to a second one of said finger members, constructed and arranged to effect high pinch force between said finger members;
    battery means for supplying electrical power to said electric motor means;
    field effect transistor driver means for actuating said electric motor to operate said myoelectrically controlled artificial hand; and
    control means for supplying myoelectric pulses to said field effect transistor driver means in response to said myoelectric signals generated by the user, thereby effecting said selective separation and convergence of said finger members.

2. The myoelectrically controlled artificial hand of claim 1 wherein said first drive train comprises a plurality of first gear members movably engaged with said high speed low torque electric motor, with each other and with said first finger member so as to effect selective separation and convergence of said first one of said finger member with said second one of said finger members and said second drive train comprises a plurality of second gear members movably engaged with said low speed high torque electric motor, with each other and with said second finger member so as to effect selective pinching of and separation of said second one of said finger members with said first one of said finger members.

3. The myoelectrically controlled artificial hand of claim 1 wherein said processor includes means for selectively actuating said high speed low torque electric motor in a first mode to close said first one of said finger members from said second one of said finger members and in a second mode to effect separation of said first one of said finger members from said second one of said finger members.

4. The myoelectrically controlled artificial hand of claim 1 wherein said processor includes means for selectively actuating said low speed high torque motor in a first mode to effect pinching of said second one of said finger members with said first one of said finger members and in a second mode to effect return of said second one of said finger members to its original position.

5. The myoelectrically controlled artificial hand of claim 1 wherein said control means comprises:
- a plurality of electrode members affixable to the user proximate a plurality of voluntary muscles of the user;
- a signal detector for detecting myoelectric signals from said electrode members;
- a processor for processing said myoelectric signals into a plurality of myopulse signals suitable for actuating said field effect transistor driver means; and
- a threshold means for restricting generation of said myoelectric pulses to those instances in which the amplitude of said myoelectric signals is greater than a specified threshold.

6. The myoelectrically controlled artificial hand of claim 5 wherein said field effect transistor driver means, said signal detector, said processor and said threshold are affixed to a module selectively removable from and connectable to said myoelectrically controlled artificial hand, for repair or replacement as desired.

7. The myoelectrically controlled artificial hand of claim 5 wherein said battery means is selectively removable from and connectable to said myoelectrically controlled artificial hand for recharging or replacement as desired.

8. The artificial hand as described in claim 1 wherein said field effect transistor driver means comprises:
- a vertical metal oxide semiconductor transistor requiring a voltage of 40–70 millivolts when driving said electric motor means, said vertical metal oxide semiconductor transistor being effective to reduce the voltage required to drive said electric motor means, from that required when using a conventional bi-polar transistor driver for operating said artificial hand.

9. The artificial hand as described in claim 1 and further comprising:
- a thermoplastic covering encompassing said finger members and said pivot member and formed in the shape of a hand so as to simulate the appearance and function of a natural hand.

10. A control mechanism for an artificial hand having a pair of pivotally mounted fingers and electric motor means for effecting said selective separation and convergence of said finger members, said control mechanism comprising:
- a plurality of electrode members affixable to a user proximate a plurality of voluntary muscles of the user;
- a signal detector for detecting said myoelectric signals and for amplifying said signal;
- a pair of dual comparators constructed and arranged for receiving said myoelectric signals, for comparing said myoelectric signals to signals of selected upper and lower threshold levels, and for generating a myopulse signal in response to myoelectric signals within said threshold levels;
- a first one of said dual comparator being effective to activate said electric motor means to separate said finger member;
- a second one of said dual comparators being effective to activate said electric motor means to converge said finger members;
- field effect transistor driver means for selectively activating and deactivating said electric motor means in response to said myopulse signals;
- damping means for selectively damping said electric motor means upon deactivation thereof; and
- switching means for limiting the pivotal motion of said pair of fingers to a selected range.

11. The control mechanism as disclosed in claim 10 and further comprising a first module affixable the forearm of the patient, said dual comparators and said field effect driver means attached thereto, and
- a second module positioned on the artificial hand of the patient and said damping means and switching means hung attached thereto; and quick disconnect electrical leads connecting said first module and said second module whereby single motor, double motor and hook type hands may be selectively attached or detached from the forearm of the patient, as desired.

12. The control mechanism as described in claim 10 wherein said switching means includes:
- means for cutting off current to a first motor when said first motor ceases to rotate, due to said first one of said finger members converging with said second one of said finger members.

13. The control mechanism as described in claim 10 wherein said switching means further includes means for cutting off current to each of said motors when each of said finger members reaches a selected position of extension.

* * * * *

UNITED STATES PATENT AND TRADEMARK OFFICE
CERTIFICATE OF CORRECTION

PATENT NO. : 4,623,354
DATED : November 18, 1986
INVENTOR(S) : Childress, et al.

It is certified that error appears in the above-identified patent and that said Letters Patent is hereby corrected as shown below:

Column 6, Line 13, after "to" delete "/".

Column 6, Line 16, change "an" to --a--.

Column 6, Line 20, change "resistor" to --resistors--.

Column 6, Line 25, change "to", first occurrence, to --too--.

Column 6, Line 65, change "directions" to --direction--.

Column 7, Line 31, change "pull" to --pulled--.

Column 7, Line 51, change "V= $(V_M + V_S)$" to --V= - $(V_M + V_S)$--.

Column 8, Line 6, change "to" to --in--.

Column 12, Line 33, after "affixable", add --to--.

Signed and Sealed this

Third Day of January, 1989

Attest:

DONALD J. QUIGG

*Attesting Officer*        *Commissioner of Patents and Trademarks*